United States Patent
Sato

(10) Patent No.: US 12,105,082 B2
(45) Date of Patent: Oct. 1, 2024

(54) TARGET SUBSTANCE SEPARATION METHOD AND QUANTIFICATION METHOD

(71) Applicant: TERUMO KABUSHIKI KAISHA, Tokyo (JP)

(72) Inventor: Hiroya Sato, Sumida-ku (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 703 days.

(21) Appl. No.: 17/236,705

(22) Filed: Apr. 21, 2021

(65) Prior Publication Data

US 2021/0239684 A1 Aug. 5, 2021

Related U.S. Application Data

(63) Continuation of application No. PCT/JP2019/040657, filed on Oct. 16, 2019.

(30) Foreign Application Priority Data

Oct. 26, 2018 (JP) ................................ 2018-201908

(51) Int. Cl.
*G01N 33/537* (2006.01)
*G01N 27/447* (2006.01)
*G01N 33/543* (2006.01)

(52) U.S. Cl.
CPC ..... *G01N 33/537* (2013.01); *G01N 27/44726* (2013.01); *G01N 27/44786* (2013.01); *G01N 33/54326* (2013.01)

(58) Field of Classification Search
CPC .......... G01N 33/537; G01N 27/44726; G01N 27/44786; G01N 33/54326; G01N 33/561; G01N 27/44769
See application file for complete search history.

(56) References Cited

U.S. PATENT DOCUMENTS 6,007,690 A * 12/1999 Nelson ............. G01N 27/44743
204/600
6,027,945 A 2/2000 Smith et al.
(Continued)

FOREIGN PATENT DOCUMENTS

| CN | 102539800 A | 7/2012 |
|---|---|---|
| CN | 105229145 A | 1/2016 |

(Continued)

OTHER PUBLICATIONS

Okamoto, Y. et al. "Online concentration and affinity separation of biomolecules using multifunctional particles in capillary electrophoresis under magnetic field." Analytical chemistry vol. 79,8 (2007): 3041-7. doi: 10.1021/ac061693q (Year: 2007).*

(Continued)

*Primary Examiner* — Aaron J Kosar
*Assistant Examiner* — Andrew T Moehlman
(74) *Attorney, Agent, or Firm* — Foley & Lardner LLP

(57) ABSTRACT

A method for separating a target substance includes: forming a mixture containing: a target substance-magnetic particle complex that includes: a sample containing a target substance, and magnetic particles to which a first receptor is fixed, wherein the first receptor is adapted to specifically recognize a site of the target substance; and separating the target substance-magnetic particle complex from the mixture by magnetism and electrophoresis.

6 Claims, 4 Drawing Sheets

(56) References Cited

U.S. PATENT DOCUMENTS

| | | | |
|---|---|---|---|
| 2008/0026222 A1 | 1/2008 | Tamori et al. | |
| 2012/0077184 A1* | 3/2012 | Hu | C12Q 1/6825 435/7.1 |

FOREIGN PATENT DOCUMENTS

| | | | |
|---|---|---|---|
| JP | H11-509742 A | 8/1999 |
| JP | 2005-233944 A | 9/2005 |
| JP | 2006-090825 A | 4/2006 |
| JP | 2007-262114 A | 10/2007 |
| JP | 2008-002959 A | 1/2008 |
| JP | 2008-032411 A | 2/2008 |
| JP | 2009-065880 A | 4/2009 |
| JP | 2009-219388 A | 10/2009 |
| JP | 2011-075539 A | 4/2011 |
| JP | 2012-042456 A | 3/2012 |
| JP | 2012-177691 A | 9/2012 |
| JP | 2014-145680 A | 8/2014 |
| JP | 2014-226093 A | 12/2014 |
| JP | 2017-044674 A | 3/2017 |

OTHER PUBLICATIONS

Chen et al. ("Magnetic beads based immunoaffinity capillary electrophoresis of total serum IgE with laser-induced fluorescence detection." Analytical chemistry vol. 80,24 (2008): 9583-8. doi: 10.1021/ac801859e (Year: 2008).*

Henken, R.L. et al. "Influence of immobilized biomolecules on magnetic bead plug formation and retention in capillary electrophoresis." Electrophoresis vol. 33,5 (2012): 827-33. doi: 10.1002/elps.201100353 (Year: 2012).*

International Searching Authority, "Written Opinion," issued in connection with International Patent Application No. PCT/JP2019/040657, dated Dec. 10, 2019.

Chen et al., "Capillary electrophoresis immunoassay using magnetic beads," Electrophoresis, vol. 29, No. 16, 2008, pp. 3414-3421.

International Searching Authority, "International Search Report," issued in connection with International Patent Application No. PCT/JP2019/040657, dated Dec. 10, 2019.

Chinese Office Action issued in CN Appl. Ser. No. 201980070299.9, dated Dec. 1, 2022.

Chinese Office Action issued in connection with CN Appl. Ser. No. 201980070299.9 dated Jun. 3, 2023.

Chen et al., "Magnetic Beads Based Immunoaffinity Capillary Electrophoresis of Total Serum IgE with Laser-Induced Fluorescence Detection", Anal. Chem. 80: (24): 9583-9588 (2008).

Extended European Search Report issued in corresponding European Patent Application No. 19874815.4, dated Oct. 27, 2021.

Hayes, et al., "Flow-Based Microimmunoassay", Anal. Chem. 73(24): 5896-5902 (2001).

Tennico et al., "In-line extraction employing functionalized magnetic particles for capillary and microchip electrophoresis", Electrophoresis 31(15):2548-2557 (2010).

* cited by examiner

TARGET SUBSTANCE SEPARATION METHOD AND QUANTIFICATION METHOD

CROSS-REFERENCE TO RELATED APPLICATIONS

This application is a bypass continuation of PCT Application No. PCT/JP2019/040657, filed on Oct. 16, 2019, which claims priority to Japanese Application No. 2018-201908, filed on Oct. 26, 2018. The contents of these applications are hereby incorporated by reference in their entireties.

BACKGROUND

This disclosure relates to a separation method and a quantification method for a target substance.

Some peptides present in a living body vary in amount due to a disease. These peptides can be markers for specific diseases. For example, diabetes is a disease in which a glucose level in blood (blood glucose level) is high due to a decrease in an action of insulin or insufficient secretion of insulin. When a high blood glucose level persists fora long period of time, the kidney, retina, and peripheral nerve can be damaged, the blood vessels can be damaged, and arteriosclerosis can be accelerated, which is a risk factor for myocardial infarction and cerebral infarction. Therefore, it is important to grasp the blood glucose level and a blood component concentration of factors related to diabetes in diagnosis, prevention, and treatment of diabetes. For example, JP-A-2014-145680 describes a method of forming a complex containing a target substance (for example, blood C-peptide, which is a constituent substance of proinsulin) and a receptor using two types of receptors having a large molecular weight, and separating the complex and a free receptor by a molecular weight difference in electrophoresis.

SUMMARY

A preferred protein as a receptor has a predetermined charge. However, depending on a magnitude relationship between the receptor and the target substance in terms of the charge and the molecular weight, it may be difficult to clearly separate the complex and the receptor even by the method disclosed in JP-A-2014-145680.

Certain embodiments of the present invention have been developed in view of the above circumstances, and an object of certain embodiments is to provide a means of separating a target substance.

The inventor has conducted intensive studies in order to solve the above problems. As a result, it has been found that the above problems can be solved by separation combining electrophoresis and magnetism.

According to one embodiment, a method for separating a target substance include: forming a target substance-magnetic particle complex using a sample containing a target substance and magnetic particles to which a first receptor that specifically recognizes a site of the target substance is fixed; and separating the target substance-magnetic particle complex by magnetism and electrophoresis.

BRIEF DESCRIPTION OF THE DRAWINGS

In FIGS. 1A and 1B, 2 and 3 denote electrodes, 4 denotes a reagent, 5 denotes an electrophoretic base material, 6 denotes a substrate, 7 denotes a sample containing a target substance, and 8 denotes a magnet.

In FIGS. 1C and 1D, 2 and 3 denote electrodes, 5 denotes an electrophoretic base material, 6 denotes a substrate, 8 denotes a magnet, and 9 denotes a target substance-magnetic particle-labeled substance complex.

FIG. 3 is a photograph of an electrophoresis device used in the Examples (Electrophoresis).

DETAILED DESCRIPTION

Figure 1A:
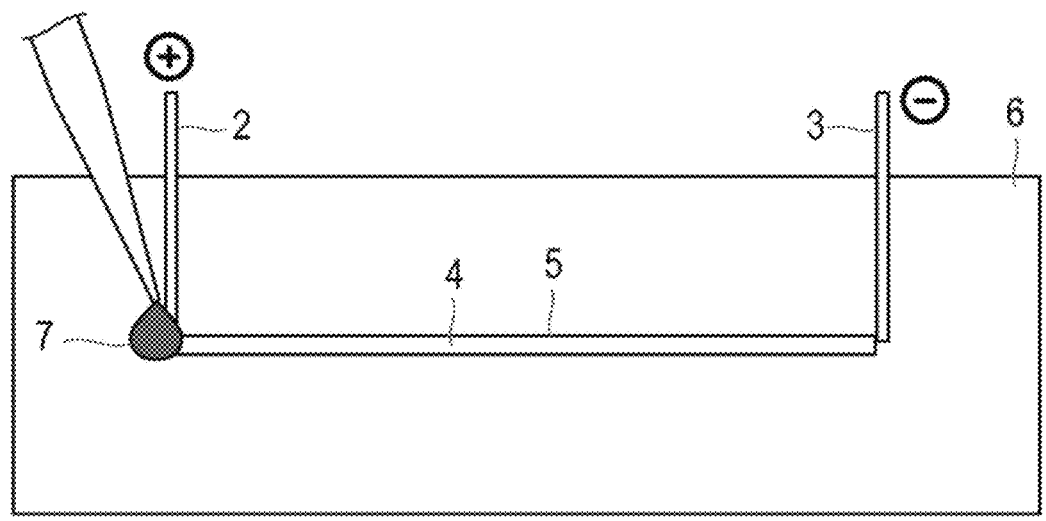
FIGS. 1A and 1B are diagrams illustrating steps of a method according to an embodiment of the present disclosure.

Example embodiments of the present disclosure will be described below. However, the invention is not limited to the following embodiments.

A first embodiment according to the present disclosure is a separation method for a target substance, including: forming a target substance-magnetic particle complex using a sample containing a target substance and magnetic particles to which a first receptor that specifically recognizes a site of the target substance is fixed; and separating the target substance-magnetic particle complex by magnetism and electrophoresis. According to this embodiment, the target substance can be separated regardless of types of the target substance (for example, a charge and a molecular weight). In addition, according to this embodiment, it is possible to separate a target substance that is difficult to detect.

A second embodiment according to this disclosure is a measurement method for a target substance amount, including: mixing a sample containing a target substance, magnetic particles to which a first receptor that specifically recognizes a site of the target substance is fixed, and a labeled substance to which a second receptor that specifically recognizes a site different from the site of the target substance is fixed to obtain a mixture containing a target substance-magnetic particle-labeled substance complex; and detecting signal intensity of the target substance-magnetic particle-labeled substance complex after separating the target substance-magnetic particle-labeled substance complex by magnetism and electrophoresis. According to this embodiment, a target substance amount can be measured with high accuracy regardless of the types of the target substance (for example, a charge and a molecular weight). In addition, according to this embodiment, the target substance amount can be measured with high accuracy even if the target substance is difficult to detect.

In the present description, a "first receptor that specifically recognizes a site of the target substance" is also simply referred to as a "first receptor." "Magnetic particles to which a first receptor that specifically recognizes a site of the target substance is fixed" are also simply referred to as "first receptor-fixed magnetic particles" or "magnetic particles according to this disclosure." A "second receptor that specifically recognizes a site different from the site of the target substance" is also simply referred to as a "second receptor." The expression "second receptor that specifically recognizes a site different from the site of the target substance" means that the second receptor specifically recognizes a site different from the site of the target substance recognized by the first receptor. A "labeled substance to which the second receptor that specifically recognizes a site different from the site of the target substance is fixed" is also simply referred to as a "second receptor-fixed labeled substance" or "labeled substance according to this disclosure."

In the present description, the expression "X to Y" indicating a range includes X and Y, and means "X or more and Y or less." Unless otherwise specified, operation and measurement for physical properties are performed under conditions of room temperature (20° C.; to 25° C.) and relative humidity of 40% to 50% RH. However, the conditions are not limited to thereto.

Separation Method for Target Substance (First Embodiment of Disclosure)

The first embodiment according to this disclosure is a separation method for a target substance, including: forming a target substance-magnetic particle complex using a sample containing a target substance and magnetic particles to which a first receptor that specifically recognizes a site of the target substance is fixed; and separating the target substance-magnetic particle complex by magnetism and electrophoresis.

According to the method of this disclosure, the complex containing the target substance and the magnetic particles (the target substance-magnetic particle complex) is formed via the first receptor. The magnetic particles contained in the complex are captured at a predetermined position by magnetism. Therefore, when electrophoresis is performed while or after the complex is captured by the magnetism, the complex remains fixed at the predetermined position by magnetism and does not move. However, components other than the complex (for example, a living-body-derived component such as blood cells) move or do not move. Therefore, the target substance (the target substance-magnetic particle complex) can be selectively separated and recovered. Since the method of this disclosure is a method of recovering a target substance of interest using the magnetic particles, the target substance can be efficiently separated regardless of the types of the target substance (for example, a charge, an isoelectric point or a molecular weight).

The first embodiment according to this disclosure will be described below.

(Sample Containing Target Substance)

The target substance is appropriately selected in accordance with purposes (types of the disease to be diagnosed). Therefore, the target substance is not particularly limited. Specifically, examples include insulin, an insulin precursor (for example, C-peptide), glucagon-like peptide-1 (GLP-1), glucoseotropic insulinotropic polypeptide (GIP), adiponectin, heart-type fatty acid binding protein (H-FABP), myoglobin, Troponin I, Troponin T, brain natriuretic peptide (BNP), N-terminal pro-brain natriuretic peptide (NT-ProBNP), proteins such as a fatty acid binding protein, peptides, sugar chains, nucleic acids, low molecular weight compounds, high molecular weight compounds, and complexes thereof. Among these, from the viewpoint of advantageousness and generality, the target substance is preferably a protein or a peptide, and more preferably a protein or a peptide (for example, insulin, and C-peptide) used for testing body fluids such as blood and urine. The protein or the peptide includes a protein or peptide that is bound to other substances such as free forms, modified forms modified with a phosphate group, a methyl group, an acetyl group, a sugar chain, a lipid, a nitrile group, and the like, salts formed of acids (for example, inorganic acids or organic acids) and bases (for example, alkali metal salts), or a nuclear protein bound to a nucleic acid. In addition, the protein may be naturally derived or a synthetic product. In the present description, the term "protein" means a polypeptide of 10 kDa or more, and a peptide means a polypeptide of less than 10 kDa.

The sample containing the target substance is not particularly limited as long as the sample contains the desired target substance as described above. Specifically, examples thereof include a test sample (blood, plasma, serum, tissue, joint fluid, urine, lymph, and the like), a cell (cultured cells, cell lines, and the like), a culture supernatant thereof, an extract thereof, and a partially purified fraction thereof. Here, an origin of the test sample is not particularly limited, and the test sample may be derived from human or mammals other than human (for example, rodents such as rats, mice, hamsters, and guinea pigs; livestock such as sheep, pigs, cows and horses; pets such as rabbits, cats and dogs; and primates such as rhesus monkeys, green monkeys, cynomolgus monkeys, and chimpanzees). In addition, specimens such as soil and water in various environments or extracts from the above specimens may be used. Among these, in consideration of the advantageousness (for example, diagnostic purpose), the sample containing the target substance is preferably a test sample, and more preferably blood (for example, whole blood, plasma, and serum), interstitial fluid, and urine. That is, according to a preferred embodiment of this disclosure, the sample is selected from the group consisting of blood, interstitial fluid, and urine.

The target substance may be used as it is as the test sample without purification (extraction), or may be used after purification (extraction). For example, a test sample such as biological components such as blood, plasma, serum, tissue, joint fluid, urine, and lymph of a subject may be used. At this time, the test sample may be diluted, purified, or the like. Alternatively, the target substance may be prepared by purification using a known protein purification method. Specifically, for example, by homogenizing a mammalian tissue or cell in the presence of an appropriate buffer and subjecting an obtained crude extract fraction of the tissue to chromatography such as reverse phase chromatography, ion exchange chromatography, and affinity chromatography, the target substance can be purified. Alternatively, the target substance may be a commercially available product.

(Magnetic Particles to which First Receptor that Specifically Recognizes Site of Target Substance is Fixed)

The magnetic particles (first receptor-fixed magnetic particles) according to this disclosure are obtained by fixing magnetic particles to the first receptor (for example, on a surface thereof) that specifically recognizes a site of the target substance.

In the present description, the term "receptor" refers to a substance capable of specifically binding to the target substance. The receptor maintains binding activity to the target substance during electrophoresis (for example, in an electrophoretic buffer). In this disclosure, the first receptor specifically recognizes a certain site (site 1) in the target substance. The second receptor specifically recognizes a site (site 2) in the target substance different from the site (site 1) in the target substance recognized by the first receptor.

The receptor is not particularly limited, and examples thereof include an antibody, a fragment of an antibody that has binding activity to a target substance (antibody fragment), a nucleic acid such as a DNA aptamer, a protein, a receptor formed of proteins, a binding protein, a peptide, a biological receptor, a chemically synthesized receptor, and a sugar chain. Among these, it is preferable to use an antibody or a fragment of an antibody as the receptor in terms of, for example, a high specific binding property to the target substance. The first receptor is preferably an antibody or a fragment of an antibody that recognizes a structural unit (epitope) (epitope 1) formed of a specific sequence of the target substance. The second receptor is preferably an antibody or a fragment of an antibody that recognizes an epitope (epitope 2) different from the epitope 1. Alternatively, the second receptor may be a receptor that specifically recognizes the first receptor (including the case of a ligand).

Examples of the antibody include a monoclonal antibody, a polyclonal antibody, a single chain antibody, a modified antibody (for example, a "humanized antibody" in which only an antigen-recognizing site is humanized), a chimeric antibody, and a bifunctional antibody capable of simultaneously recognizing two epitopes. The antibody may be of any class such as IgA, IgD, IgE, IgG, and IgM. From the viewpoint of the specific binding property to the epitope, it is preferable to use a monoclonal antibody, and it is more preferable to use an IgG monoclonal antibody.

Examples of the fragment of an antibody (fragment) include a Fab fragment, a Fab' fragment, a F (ab)'2 fragment, a single strand antibody (scFv), scFv-Fc, genetically engineered conjugated molecules such as a minibody and a diabody, or derivatives thereof modified with a molecule having a protein stabilizing effect such as polyethylene glycol (PEG). The receptor may be an antibody treated with various proteases, or may have any label (tag) in accordance with the purpose.

The receptor that binds to the target substance can be prepared by a known method in the related art. For example, the monoclonal antibody can be prepared by the following procedure. First, an antigen alone or together with a carrier and a diluent is administrated to a site where an antibody can be produced by administration of an animal antigen. A complete Freund's adjuvant or an incomplete Freund's adjuvant may be administrated in order to enhance antibody production capacity during the administration. Examples of the animals used include mammals such as monkeys, rabbits, dogs, guinea pigs, mice, rats, sheep and goats. An antibody titer in an antiserum can be measured by a method in the related art. An individual with a known antibody titer is selected from animals immune to the antigen, the spleen or lymph node thereof is collected two to five days after final immunization, and an antibody-producing cell contained therein is fused with a myeloma cell, whereby a monoclonal antibody-producing hybridoma can be prepared. A fusion operation can be performed according to a known method, for example, the method described in Nature 256: 495 (1975). Examples of a fusion accelerator include polyethylene glycol (PEG). Examples of the myeloma cell include NS-1, P3U1, and SP2/0. The selection of the monoclonal antibody can be performed according to a known method or a method similar thereto. Generally, the selection can be performed in an animal cell medium added with hypoxanthine-aminopterin-thymidine (HAT) or the like. Any medium can be used as a medium for selection and breeding as long as the hybridoma can grow. The antibody titer of a hybridoma culture supernatant can be measured in the same manner as the measurement of the antibody titer in the antiserum. In the same manner as the separation and purification for a general polyclonal antibody, separation and purification for the monoclonal antibody can be performed according to a separation and purification method for immunoglobulin, for example, by a salting out method, an alcohol precipitation method, an isoelectric point precipitation method, an electrophoresis method, an adsorption/desorption method by ion exchanger (for example, DEAE), an ultracentrifugation method, a gel filtration method, and a specific purification method using an antigen-binding solid phase or protein A or protein G, antigen affinity purification, and the like.

The polyclonal antibody can be prepared, for example, by the following procedure. The polyclonal antibody can by prepared by, for example, using a peptide or the like containing an epitope as an antigen to form a complex with a carrier, immunizing a mammal in the same manner as in the above monoclonal antibody preparation method, collecting an antibody-containing substance against active haptoglobin from the immune animal, and separating and purifying the antibody. When forming the complex containing the antigen and the carrier, the type of the carrier and a mixing ratio of the antigen to the carrier for crosslinking are optional as long as the antibody can be efficiently produced against the antigen crosslinked with the carrier. For example, bovine serum albumin, bovine thyroglobulin, and keyhole limpet hemocyanin are used as the carrier. Various condensing agents can be used for the coupling between the antigen and the carrier, and glutaraldehyde, carbodiimide, a maleimide active ester, an active ester reagent containing a thiol group and a dithiopyridyl group and the like are used. The complex containing the antigen and the carrier, alone or together with a carrier and a diluent, is administrated to a site where an antibody can be produced in an animal to be immunized. The complete Freund's adjuvant or the incomplete Freund's adjuvant may be administrated in order to enhance the antibody production capacity during the administration. The administration can be usually performed once every two to six weeks, for a total of about three to ten times. Examples of the animal used include mammals similar to those used in the production of the monoclonal antibody. The polyclonal antibody can be collected from blood, ascites, or the like of the animal immunized by the above method, and preferably from blood. Measurement of the polyclonal antibody titer in the antiserum can be performed in the same manner as the above-described measurement of the antibody titer in serum. Separation and purification for the polyclonal antibody can be performed in the same procedure as the above-described separation and purification for the monoclonal antibody.

A commercially available product may be used as the antibody. For example, when insulin is the target substance, examples of the commercially available product of the antibody include Monoclonal mouse anti-human (C7C9), Monoclonal mouse anti-human (D4B8), Monoclonal mouse anti-human (7F8), Monoclonal mouse anti-human (3A6), Monoclonal mouse anti-human (8E2), and Monoclonal mouse anti-human (7F5) (all manufactured by Hytest). For example, when fatty acid binding protein is the target substance, examples of the commercially available product of the antibody include Monoclonal mouse anti-human fatty acid binding protein (28), Monoclonal mouse anti-human fatty acid binding protein (25), Monoclonal mouse anti-human fatty acid binding protein (5B5), Monoclonal mouse anti-human fatty acid binding protein (9F3), Monoclonal mouse anti-human fatty acid binding protein (10E1), Monoclonal mouse anti-human fatty acid binding protein (22), and Monoclonal mouse anti-human fatty acid binding protein (30) (all manufactured by Hytest). Further, for example, when C-peptide is the target substance, examples of the commercially available product of the antibody include a combination of Anti-h C-peptide 9103 SPRN-5 (Mouse monoclonal (manufactured by Medix Biochemica Company)) with a monoclonal antibody selected from any of Monoclonal mouse anti-human C-peptide (7E10) (manufactured by abcam Company), Anti C-peptide antibody (5B8) (Mouse monoclonal (manufactured by abcam Company)), Anti C-peptide antibody (2B7) (Mouse monoclonal (manufactured by abcam Company)), Anti-C-peptide antibody (2A11) (Mouse monoclonal (manufactured by abnova Company)), and Anti-h C-peptide 9101 SPIN-5 (Mouse monoclonal (manufactured by Medix Biochemica Company)), or a combination of Anti C-peptide antibody (2A11) (Mouse monoclonal (manufactured by abnova Company)) with Anti C-peptide antibody (4H8) (Mouse monoclonal (manufactured by abcam Company)), and of Anti C-peptide antibody (4H8) (Mouse monoclonal (manufactured by abcam Company)) with Anti C-peptide antibody (5B8) (Mouse monoclonal (manufactured by abcam Company)).

The magnetic particles (magnetic particles before the first receptor is fixed thereto) are not particularly limited as long as the magnetic particles have magnetism. For example, the magnetic particles are formed of magnetic materials such as ferrite represented by $MFe_2O_4$ (M=Co, Mn, Ni, Mg, Cu, Zn, $Li_{0.5}Fe_{0.5}$, and the like), maghemite ($\gamma$-$Fe_2O_3$), magnetite ($Fe_3O_4$), nickel zinc ferrite ($Ni_{1-x}Zn_xFe_2O_4$), manganese zinc ferrite ($Mn_{1-x}Zn_xFe_2O_4$), metals such as iron, manganese, nickel, cobalt, and chromium, and alloys of cobalt, nickel, manganese or the like. Among these, $\gamma$-$Fe_2O_3$ and $Fe_3O_4$ are preferred from the viewpoint of high saturation magnetization and low residual magnetization. An average particle size (primary particle size) of the magnetic particles is not particularly limited, and can be appropriately selected in accordance with electrophoresis conditions (for example, an inner diameter of an electrophoretic base material, and compatibility with an electrophoresis buffer) and the like. From the viewpoint of mobility, dispersibility and sufficient magnetic force during electrophoresis, the average particle size (primary particle size (diameter)) of the magnetic particles is preferably 50 nm to 20 μm, more preferably 100 nm to 10 μm, and particularly preferably 1 μm to 5 μm. The term "particle size" means a maximum distance between any two points on a contour line of the magnetic particle. In the present description, the term "average particle size" means a value calculated by extracting 300 or more particles in a photograph taken by a scanning electron microscope (SEM), a transmission electron microscope (TEM), or an optical microscope, measuring diameters of these particles, and averaging the diameters.

A surface of the magnetic particle may be coated with a polymer or the like. Here, the polymer is not particularly limited, and a known polymer used in biochemical fields (for example, a carrier, a polymer bead, and a magnetic particle) can be used in the same manner or with appropriate modifications. Specifically, examples thereof include radically polymerizable polymers such as a (meta)acrylate-based polymer and a styrene-based polymer. Among these, a polymer having a hydrophobic surface such as polystyrene and polycyclohexylmethacrylate that can be bound to a biochemical substance, and a polymer having surface functional groups such as a carboxyl group and a tosyl group can be preferably used. In the present description, the term "(meta)acrylate" includes both "acrylate" and "methacrylate." When the surface of the magnetic particle is coated with a polymer or the like, a coating film may have at least one polar group selected from the group consisting of an amino group, an aldehyde group, a carboxy group, a tosyl group, a mercapto group, a hydroxy group, and an epoxy group. In such a case, the target substance or the receptor such as an antibody can be easily bound to (carried on) the magnetic particles via the polar group.

In place of or in addition to the above coating, the magnetic particles may have a modifying substance fixed on the surface thereof. Here, the modifying substance is not particularly limited, and can be appropriately selected in accordance with a desired use. Specifically, examples thereof include proteins such as biotin, avidin, streptavidin, neutravidin, protein A, protein G, protein L, antigens, antibodies, and enzymes; nucleic acids such as DNA and RNA; and small molecule compounds such as small molecule drugs, physiologically active substances, oligopeptides, oligonucleotides, and lipids. By being modified with such a modifying substance, binding to the receptor can be facilitated. Here, a method of fixing (modifying) the modifying substance on the magnetic particles is not particularly limited. For example, methods disclosed in JP-A-2007-262114, JP-A-2008-32411 (corresponding to US 2008/026222 A1), JP-A-2012-177691 can be applied in the same manner or with appropriate modifications.

Alternatively, the magnetic particles may be a commercially available product. As the magnetic particles to be used, a bead in which a plurality of magnetic substances such as a magnetic bead and a magnetic agarose bead are coated with a polymer or a gel (for example, methacrylate and dextran) may be used. The magnetic particles to be used may be magnetic particles appropriately modified in accordance with the purpose, such as an antibody-bound magnetic bead and a tag antibody-bound bead. Specifically, examples thereof include streptavidin-labeled magnetic beads such as Magnosphere™ MS300/Streptavidin, Magnosphere™ MS160/Streptavidin, Magnosphere™ SS150/Streptavidin, and Magnosphere™ SS550/Streptavidin (all manufactured by JSR Life Sciences Company), carboxylic acid group-introduced magnetic beads such as Magnosphere™ MS300/Carboxyl, Magnosphere™ MS160/Carboxyl, Magnosphere™ MX200/Carboxyl, Magnosphere™ SS150/Carboxyl, and Magnosphere™ SS550/Carboxyl (all manufactured by JSR Life Sciences Company), and tosyl group-introduced magnetic beads such as Magnosphere™ MS300/Tosyl and Magnosphere™ MS160/Tosyl.

A method of fixing the first receptor to the surface of the magnetic particles is also not particularly limited. Known methods including: a specific binding pair labeling method that chemically binds a substance that exhibits a specific binding property to a paired substance, such as a method of labeling a receptor (for example, an antibody) with biotin and binding the biotin-labeled receptor to a streptavidin-labeled magnetic bead, and a method of labeling a receptor (for example, an antibody) with streptavidin and binding the streptavidin-labeled receptor to a biotin-labeled magnetic bead; an NHS method of forming a —COO—NHS group on a bead surface by selectively activating a carboxylic group of a carboxylic acid group-introduced magnetic bead by N-hydroxysuccinimide (NHS), and binding to a receptor (for example, an antibody) via the —COO—NHS group; a maleimide method of forming a sulfhydryl group (—SH) by reducing a disulfide bond of a receptor (for example, an antibody) with a reducing agent while introducing a maleimide group onto a surface of the magnetic particle, and reacting the maleimide group with the sulfhydryl group of the receptor; a periodic acid method of oxidizing a sugar chain part of an enzyme with periodic acid, introducing an aldehyde group, reacting the aldehyde group with an amino group of a receptor (for example, an antibody) to form a Schiff base (—CH=N—), and reducing the Schiff base to —CH₂NH—; and a glutaraldehyde method of treating an enzyme with excess glutaraldehyde, introducing an aldehyde group, reacting the aldehyde group with an amino group of a receptor (for example, an antibody) to form a Schiff base (—CH=N—), and reducing the Schiff base to —CH₂NH—, can be used in the same manner or with appropriate modifications.

A usage amount of the first receptor-fixed magnetic particles according to this disclosure is not particularly limited and is appropriately selected in accordance with a target substance amount, whereas the usage amount is usually larger than the target substance amount. The usage amount of the first receptor-fixed magnetic particles according to this disclosure is an amount such that preferably 1 mol to 10000 mol, more preferably more than 1 mol to 1000 mol, and particularly preferably 10 mol to 1000 mol of the first receptor (for example, an antibody) is present with respect to 1 mol of the target substance. When two target substances bind to one magnetic particle (for example, in a magnetic particle to which an IgG antibody is fixed), the amount of the first receptor-fixed magnetic particles is twice the preferred amount in weight. The target substance amount can be predicted to some extent by those skilled in the art, such as an insulin amount contained in blood, and an upper limit of a predicted range is set as the target substance amount. When the target substance amount cannot be predicted by those skilled in the art, an excess amount of the first receptor (for example, 0.1 μg/mL to 100 μg/mL of the first receptor in a reaction solution) may be used.

(Formation of Target Substance-Magnetic Particle Complex)

By mixing the sample containing the target substance with the magnetic particles (first receptor-fixed magnetic particles) according to this disclosure, the target substance and the magnetic particles are bound to each other via the first receptor to form a target substance-magnetic particle complex. A formation condition of the target substance-magnetic particle complex at this time is not particularly limited as long as the desired complex is formed. For example, the sample containing the target substance and the first receptor-fixed magnetic particles are mixed in a buffer solution. Here, the buffer solution is not particularly limited, and a known buffer solution can be used. Specifically, examples thereof include: solutions containing organic acids such as citric acid, succinic acid, tartaric acid, malic acid, and salts thereof; and solutions containing amino acids such as glycine, taurine and arginine, and inorganic acids such as hydrochloric acid, nitric acid, sulfuric acid, phosphoric acid, boric acid and acetic acid, and salts thereof. Specifically, examples of an electrophoretic buffer solution include good buffers (a Tris-glycine buffer solution, a Tris buffer solution, a Tris-tricine buffer solution, a Bis-Tris buffer solution, a PIPES buffer solution, a Tris-hydrochloric (Tris-HCl) buffer solution, an MOPS buffer solution, an HEPES buffer solution, a PIPES buffer solution, an ACES buffer solution, an MOPSO buffer solution, BES buffer solution, a TES buffer solution, a DIPSO buffer solution, TAPSO buffer solution, a POPSO buffer solution, an HEPPSO buffer solution, an EPPS buffer solution, a TAPS buffer solution, Bicine buffer solution, a CHES buffer solution, a CAPSO buffer solution, a CAPS buffer solution, and the like), a phosphate buffer solution (PBS), an acetate buffer solution, a carbonate buffer solution, and a glycine buffer solution. The buffer solution may be used alone or in the form of a mixture containing two or more solutions. The buffer solution may contain stabilizers such as EDTA, bovine serum albumin (BSA), casein and polyethylene glycol, and nonionic surfactants such as Tween and Triton-X. A pH of the buffer solution is not particularly limited as long as the receptor is under an environment that maintains the target substance binding activity. In consideration of the ability of the receptor to maintain the binding activity to the target substance, the pH is usually preferably about neutral to weakly basic. From such a viewpoint, the pH of the buffer solution is more preferably 6.0 to 9.0, and particularly preferably 6.0 to 8.0. A mixing temperature is preferably from 4° C.; to 40° C., and more preferably from 4° C.; to 25° C. A mixing time is preferably 1 to 72 hours, and more preferably 8 to 24 hours. Alternatively, the mixing time is preferably 1 to 60 minutes, and more preferably 5 to 30 minutes.

By mixing (reacting) the sample containing the target substance with the magnetic particles (first receptor-fixed magnetic particles) according to this disclosure, a reaction solution containing a target substance-magnetic particle complex in which one or two target substances are bound to one magnetic particle (when a reducing antibody is used, a target substance-magnetic particle complex in which one target substance is bound to one magnetic particle) and unreacted magnetic particles is obtained.

(Separation of Target Substance-Magnetic Particle Complex)

The target substance-magnetic particle complex thus formed is separated by magnetism and electrophoresis. That is, the magnetic particles contained in the target substance-magnetic particle complex are captured at a predetermined position by magnetism. Therefore, when electrophoresis is performed while or after the complex is captured by magnetism, the complex remains fixed at the predetermined position by magnetism, and components other than the complex (for example, a living-body-derived component such as blood cells) move or do not move at all. Hence, according to the method in this disclosure, the target substance (target substance-magnetic particle complex) can be efficiently separated and recovered regardless of types of the target substance, or even in the case of a target substance that is difficult to detect. The target substance-magnetic particle complex may be in a form of being contained in a buffer solution as obtained in the above (Formation of Target Substance-Magnetic Particle Complex), or may be in a form of being separated from a buffer solution, or may be in a form of being separated from a buffer solution and then dispersed in another buffer solution.

Electrophoresis is not particularly limited, and known electrophoresis can be used. Specifically, examples thereof include: gel electrophoresis such as agarose gel electrophoresis, pulsed-field gel electrophoresis (PFGE), and polyacrylamide gel electrophoresis (PAGE); isoelectric point electrophoresis having a pH gradient formed in the electrophoresis gel; two-dimensional electrophoresis, which is a combination of isoelectric point electrophoresis (first dimension) and SDS-polyacrylamide gel electrophoresis (SDS-PAGE); carrier electrophoresis such as denaturing gradient gel electrophoresis (DGGE) using urea or formamide as a denaturant; and carrier-free electrophoresis such as carrier-free isoelectric point electrophoresis and microchip electrophoresis. In the above carrier electrophoresis, in addition to the above, a gel such as dextran may be used instead of a carrier such as a capillary polymer described below. Among these, the carrier-free electrophoresis is preferred for the following reasons. For example, when the carrier electrophoresis is performed using blood (whole blood) as a sample, a blood cell pool can be formed at a boundary surface between the sample and the carrier (for example, gel). In the blood cell pool, an influence on the measurement of the target substance can be eliminated if the target substance in a general concentration range (for example, when the target substance is contained in the sample in an order from mM to µM) is detected. However, when a trace amount of fluorescence is present in the target substance, when detecting the fluorescence, the protein and the like in blood cells contained in the blood cell pool at the boundary surface between the sample and the carrier fluoresce (autofluorescence), so that a large noise is generated, which causes a decrease in sensitivity. In the case of electrophoresis using a carrier, a part of the target substance-receptor complex remains in the blood cell pool, which may cause signal reduction. On the other hand, in the case of carrier-free electrophoresis, the blood cell pool cannot be formed since no boundary surface is present between the sample and the carrier. Blood cells are electrophoresed (usually on a positive side) by electrophoresis. That is, auto fluorescence caused by blood cells, which is one of the causes for the decrease in sensitivity, can be reduced and prevented. Therefore, highly sensitive measurement can be achieved. Further, since a carrier is not used in carrier-free electrophoresis, a process after the separation is easy. In addition, a large amount of continuous electrophoresis is possible, and connection with other separation means is easy. That is, according to a preferred embodiment of this disclosure, the electrophoresis is carrier-free electrophoresis.

The target substance-magnetic particle complex is separated from other components by magnetism. Here, the other components to be separated mean components other than the target substance. Specifically, example thereof include components other than the target substance (for example, blood components) contained in the sample, and components of a diluent (for example, a buffer solution) (when used).

In this disclosure, a magnet is placed at a predetermined position in an electrophoresis direction. The magnet is not particularly limited as long as the magnet can capture the magnetic particles. Specifically, examples thereof include a rare earth magnet (a neodymium magnet, a bonded magnet, and the like), a ferrite magnet, and an electromagnet.

Hereinafter, embodiments in which the target substance-magnetic particle complex is separated by carrier-free electrophoresis and magnetism will be described with reference to the drawings. This disclosure is not limited to the following embodiments.

FIGS. 1A to 1D are diagrams illustrating steps of a method according to this disclosure.

First, as shown in FIG. 1A, an electrophoretic base material (for example, a capillary) 5 is filled with a reagent 4 containing first receptor-fixed magnetic particles. The electrophoretic base material 5 is arranged on a substrate 6 of an electrophoresis device. Electrodes (for example, platinum electrodes) 2 and 3 are provided at both ends of the electrophoretic base material 5. Accordingly, an electric field is applied in a longitudinal direction of the electrophoretic base material 5. The reagent may be formed of only the first receptor-fixed magnetic particles. Alternatively, in addition to the first receptor-fixed magnetic particles, the reagent may contain pH adjusting agents (for example, sodium hydroxide, sodium carbonate, sodium hydrogen carbonate, sulfuric acid, hydrochloric acid, and phosphoric acid), buffering agents (for example, sodium hydrogen phosphate, sodium phosphate, and Tris-HCL), hemolytic agents such as saponin, and surfactants.

The electrophoretic base material 5 is not particularly limited, and is preferably transparent from the viewpoint of visibility of a flow of the complex. Specifically, the electrophoretic base material is preferably formed of a transparent material such as a transparent resin such as acrylic resin, quartz glass and synthetic quartz. From the viewpoint of less autofluorescence, an electrophoretic base material formed of quartz glass or synthetic quartz is more preferred, and an electrophoretic base material formed of synthetic quartz is particularly preferred. From the viewpoint of cost, an electrophoretic base material formed of a transparent resin is particularly preferred. A shape of the electrophoretic base material 5 is not particularly limited, and may be a cylinder, a prism, or the like. In consideration of installation stability and the like, a cross-sectional shape of the electrophoretic base material 5 is preferably a prism having a polygonal shape, particularly a quadrangular shape. A size of the electrophoretic base material 5 is also not particularly limited. In consideration of ease of the flow of the buffer and the sample and the effect of reducing and preventing electroosmotic flow (EOF), a maximum length of a cross section of the electrophoretic base material 5 (a length of one side (inner side) when the cross section is polygonal, and an inner diameter (diameter) when the cross section is circular) is preferably 0.1 mm to 2 mm, and more preferably 0.5 mm to 1 mm. In consideration of ease of separation and handling of the complex, the length of the electrophoretic base material 5 is preferably 1 cm to 10 cm, and more preferably 2 cm to 5 cm.

The substrate 6 is not particularly limited, and is preferably transparent from the viewpoint of visibility of the flow of the complex. Specifically, the substrate is preferably formed of a transparent material such as a transparent resin such as acrylic resin, quartz glass and synthetic quartz. From the viewpoint of less auto fluorescence, a substrate formed of quartz glass or synthetic quartz is more preferred, and a substrate formed of synthetic quartz is particularly preferred. From the viewpoint of cost, the substrate 6 formed of a transparent resin is particularly preferred.

Next, as shown in FIG. 1A, a sample 7 containing a target substance is dropped on a platinum electrode 2 side. Accordingly, the sample 7 enters the electrophoretic base material 5 by a capillary action, and is mixed with the reagent 4. Accordingly, the target substance in the sample 7 and the first receptor present in the first receptor-fixed magnetic particles react with each other in the electrophoretic base material 5 to form a target substance-magnetic particle complex. Here, a dropping amount of the sample 7 (specimen 1) containing the target substance is not particularly limited, and is appropriately set in accordance with the size and the like of the electrophoretic base material. A reaction condition is not particularly limited, and the condition described above can be applied in the same manner. In the present embodiment, the sample 7 is dropped on a positive (+) electrode 2 side, whereas this disclosure is not limited thereto. As described above, the present embodiment is particularly preferably applied when a carboxyl group (—COOH) present in the protein is negatively charged.

An amount of the first receptor-fixed magnetic particles in the reagent is not particularly limited, and the same amount as described in the above section (Magnetic Particles to which First Receptor that Specifically Recognizes Site of Target Substance is Fixed) can be used.

In the present embodiment, the electrophoretic base material is filled with the reagent containing the first receptor-fixed magnetic particles in advance. Alternatively, after the first receptor-fixed magnetic particles and the target substance may be reacted in advance to form the target substance-magnetic particle complex, the electrophoretic base material 5 may be filled with a reaction product thereof (second embodiment). In the case of the second embodiment, it is preferable to separately provide a chamber (not shown) for the above reaction on the substrate 6. Alternatively, in another embodiment, a reagent solution containing the first receptor-fixed magnetic particles and a buffer may be dropped onto both end portions of the electrophoretic base material to form a liquid pool, the electrophoretic base material may be filled with the reagent solution by a capillarity action, the electrodes (for example, platinum electrodes) 2 and 3 may be installed at both ends of the electrophoretic base material 5, and a sample containing the target substance may be dropped onto any one of the electrodes (third embodiment). In the third embodiment, the buffer is not particularly limited as long as the receptor maintains the target substance binding activity, and the buffer solution used for general electrophoresis can be used in the same manner or with appropriate modifications. Specifically, the buffer solution is not particularly limited as long as the buffer solution is a solution containing a buffer solution composition that has buffering capacity as known in the related art. For example, examples thereof include a buffer solution similar to that exemplified in the above section (Formation of Target Substance-Magnetic Particle Complex). Alternatively, a buffer solution or the like provided in a commercially available electrophoresis kit can also be used. A buffer solution for electrophoresis can be used at a concentration generally used as an electrophoretic buffer solution. A pH of the buffer solution is not particularly limited as long as the receptor is under an environment that maintains the target substance binding activity. However, in consideration of the ability of the receptor to maintain the binding activity to the target substance, the stability and reactivity of the reagent, and the like, the pH is usually preferably around neutral to weakly basic. From such a viewpoint, the pH of the buffer solution is more preferably 6 to 9. In particular, when the target substance is a protein, since the pH of the buffer solution is on the basic side, the carboxyl group (—COOH) present in the protein is negatively charged (becomes —COO$^-$), so that the movement of the complex during electrophoresis is promoted. The pH of the buffer solution may be adjusted appropriately by using an acidic substance such as hydrochloric acid or a basic substance such as sodium hydroxide.

Figure 1B:
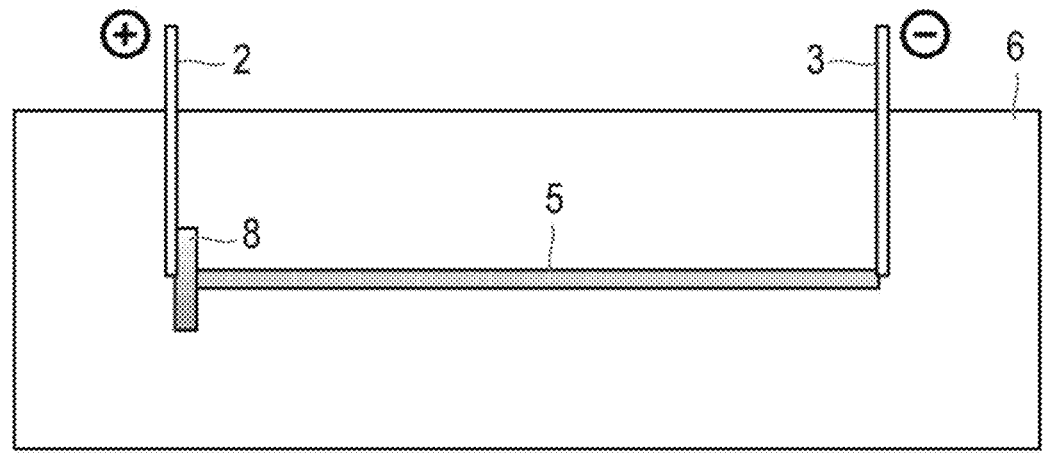
Figure 1C:
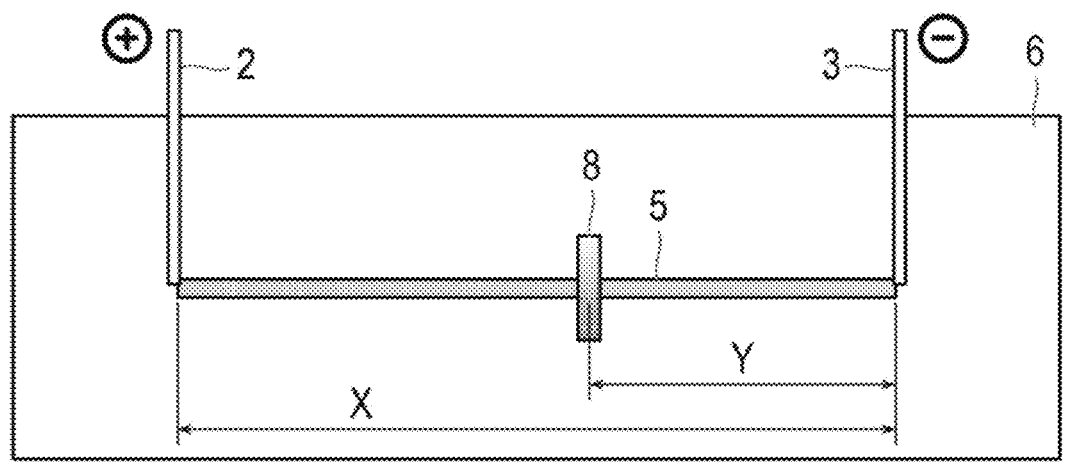
FIGS. 1C and 1D are diagrams illustrating steps of a method according to an embodiment of the present disclosure.

Next, as shown in FIG. 1B, a magnet 8 is installed on the platinum electrode 2 (anode) side of the electrophoretic base material 5. Accordingly, the magnetic particles contained in the target substance-magnetic particle complex are captured by the magnet 8. Next, as shown in FIG. 1C, after the magnet 8 is moved in the longitudinal direction of the electrophoretic base material 5, electrophoresis is started. Accordingly, the target substance-magnetic particle complex can be selectively separated. That is, according to a preferred embodiment of this disclosure, after obtaining a mixture containing the target substance-magnetic particle complex, the target substance-magnetic particle complex is captured at a predetermined position by magnetism and then subjected to electrophoresis, whereby the target substance-magnetic particle complex is separated from the mixture.

Here, although a movement position of the magnet 8 is not particularly limited, it is preferable to install the magnet 8 on a cathode side (platinum electrode 3 in FIG. 1C) of the electrophoretic base material 5. According to the present embodiment, a component to be separated from the target substance in the sample (for example, a substance that causes noise or background increase during detection (in the second embodiment below, blood cells that has autofluorescence, a substance that has fluorescence that is not to be detected, and the like)) moves to the anode side. Therefore, during the detection, a distance between the target substance-magnetic particle complex and the substance that causes noise can be increased in the electrophoretic base material 5. Therefore, the decrease in sensitivity can be reduced and prevented more effectively, and the sensitivity can be further improved by reducing the background and noise. Specifically, it is preferable to install the magnet from half the entire electrophoresis process, i.e., from an electrophoresis start point to an electrophoresis end point, away from the cathode side (position at Y/X≤½ in FIG. 1C). More preferably, the magnet is installed at a position (a position where Y/X=0 to ½ in FIG. 1C) where a distance (Y in FIG. 1C) from the cathode to the magnet is away from the cathode by half the entire electrophoresis process (Y=X in FIG. 1C) from the cathode (Y=0 in FIG. 1C) to the anode. Particularly preferably, the magnet is installed at a position where a ratio (Y/X) of the distance (Y in FIG. 1C) from the cathode to the magnet to the entire electrophoresis process (X in FIG. 1C) from the cathode to the anode is 1/10 to 3/5 (Y/X=1/10 to 3/5 in FIG. 1C). Most preferably, the magnet is installed at a position where a ratio (Y/X) of the distance (Y in FIG. 1C) from the cathode to the magnet to the entire electrophoresis process (X in FIG. 1C) from the cathode to the anode is 1/10 to 2/5 (Y/X=1/10 to 2/5 in FIG. 1C). By installing the magnet at the above position, it is possible to more effectively reduce and prevent the decrease in sensitivity such as autofluorescence. In FIG. 1C, "X" indicates a length (mm) between the cathode and the anode (corresponding to a total length of the electrophoretic base material 5).

"Y" indicates a distance (mm) from the cathode to a midpoint (center) of a width of the magnet. Further, a relationship between an installation distance of the magnet with respect to the cathode and the anode can be a relationship opposite to that of the second embodiment depending on the type of the substance to be detected.

After the magnet 8 is arranged at the predetermined position on the electrophoretic base material 5, electrophoresis is started. Here, an electrophoresis condition is not particularly limited as long as the component other than the complex (for example, impurities derived from the sample) can be separated, and general conditions can be applied. For example, an applied voltage in electrophoresis may be appropriately selected from a range that is usually used in this field, and is usually preferably 5 V to 200 V, and more preferably 10 V to 100 V, in terms of a DC voltage. An electrophoresis time can usually be 30 to 180 minutes. From the viewpoint of rapid separation, the electrophoresis time is preferably about several minutes to 10 minutes. An electrophoresis temperature is not particularly limited, and is usually performed at room temperature (20° C.; to 25° C.).

As described above, the sample immediately before electrophoresis (hereinafter, also referred to as "specimen 1") contains the target substance-magnetic particle complex and the unreacted magnetic particles in addition to the components contained in the sample (for example, a living-body-derived component such as blood cells) and the components contained in the buffer solution. In the above electrophoresis, the target substance-magnetic particle complex and the unreacted magnetic particles are captured by the magnet. In addition, usually, the magnetic particles captured at one position are visible (see, for example, FIG. 2B). Therefore, by removing only a portion of the electrophoretic base material on which the magnet is arranged by cutting or the like, the target substance can be efficiently separated from the components (for example, blood cells) contained in the sample or the buffer solution. In order to prevent diffusion of the target substance (target substance-magnetic particle complex), it is preferable to remove only the portion of the electrophoretic base material on which the magnet is arranged while the magnet remains arranged thereon.

Measurement Method for Target Substance Amount
(Second Embodiment of Disclosure)

The second embodiment according to this disclosure is a measurement method for a target substance amount, including: mixing a sample containing a target substance, magnetic particles to which a first receptor that specifically recognizes a site of the target substance is fixed, and a labeled substance to which a second receptor that specifically recognizes a site different from the site of the target substance is fixed to obtain a mixture containing a target substance-magnetic particle-labeled substance complex; and detecting signal intensity of the target substance-magnetic particle-labeled substance complex after separating the target substance-magnetic particle-labeled substance complex by magnetism and electrophoresis.

According to the method of this disclosure, the complex containing the magnetic particles, the target substance, and the labeled substance (target substance-magnetic particle-labeled substance complex) is formed by binding the target substance and the magnetic particles via the first receptor, and binding the target substance and the labeled substance via the second receptor. The magnetic particles contained in the complex are captured at a predetermined position by magnetism. Therefore, when electrophoresis is performed while or after the complex (target substance-magnetic particle-labeled substance complex) is captured by magnetism, the complex remains fixed at the predetermined position by magnetism, and components other than the complex (for example, a living-body-derived component such as blood cells or protein) move. In particular, when detecting an object to be measured using a fluorescence-labeled receptor, impurities that are not to be detected (protein, peptide, amino acid, cell membrane, fatty acid, and the like) can be electrophoresed to a cathode side or an anode side by electrophoresis. In particular, if the amino acid having fluorescence, the peptide, and the protein that is not to be detected are separated by electrophoresis, noise and background can be significantly reduced. Therefore, the target substance (target substance-magnetic particle-labeled substance complex) can be selectively separated and recovered. Since the method of this disclosure is a method of recovering the target substance of interest using the magnetic particles, the target substance can be efficiently separated regardless of the types of the target substance (for example, a charge, an isoelectric point or a molecular weight). In addition, since the target substance-magnetic particle-labeled substance complex can be selectively recovered, the target substance amount of interest can be measured with high accuracy.

Although the second embodiment of this disclosure will be described below, the description related to repeated matters (for example, the sample containing the target substance, the magnetic particles (first receptor-fixed magnetic particles), the magnet, and electrophoresis according to this disclosure) is the same as the description in the first embodiment of this disclosure, and thus a description thereof is omitted here.

(Labeled Substance to which Second Receptor that Specifically Recognizes Site Different from Site of Target Substance is Fixed)

The labeled substance (second receptor-fixed labeled substance) according to this disclosure is obtained by fixing a labeled substance to the second receptor (for example, on a surface thereof) that specifically recognizes a site different from a recognition site of the first receptor. Here, the second receptor is not particularly limited, and is the same as that described in the magnetic particles (first receptor-fixed magnetic particles) according to this disclosure. Therefore, the description thereof is omitted here. The second receptor recognizes a site different from that of the first receptor, that is, the first receptor and the second receptor (for example, an antibody) recognize different sites of one target substance. For example, when the first receptor and the second receptor recognize a fatty acid-binding protein, different receptors (for example, antibodies) are selected, for example, using the Monoclonal mouse anti-human fatty acid binding protein (25) as the first receptor and the Monoclonal mouse anti-human fatty acid binding protein (28) as the second receptor.

The labeled substance (labeled substance before the second receptor is fixed) is not particularly limited as long as the labeled substance can be used to measure a desired target substance amount in a later step. Examples thereof include a fluorescent substance, a radioactive isotope, an enzyme, and a redox substance. The labeled substance may be used alone or in combination of two or more types thereof. That is, according to a preferred embodiment of this disclosure, the labeled substance is at least one selected from the group consisting of a fluorescent substance, a radioactive isotope, an enzyme, and a redox substance. Here, the fluorescent substance is not particularly limited, and a fluorescent substance that is usually used for measuring the target substance amount can be used. Specifically, examples thereof include Alexa Flour (Life Company), Hilyte Flour (Ana Spec Company), IRDye (manufactured by LI-COR Biosciences), IRDye 800CW Maleimide (manufactured by LI-COR Biosciences), Fluorescein Isothiocyanate (FITC), phycoerythrin (PE), Allophycocyanin (APC), Cy-3, Cy-5, tetramethylrhodamine isocyanate, and semiconductor quantum dots. Among these, it is preferable to use a fluorescent dye that is excited on a long wavelength side. Since many substances that fluoresce at a short wavelength exist in nature, auto fluorescence can be reduced more effectively by using the fluorescent dye that is excited on the long wavelength side. In consideration of the above points, it is preferable to use a fluorescent dye that is excited at 700 nm to 1,000 nm, particularly at 750 nm to 900 nm. The fluorescent dye excited in such a wavelength range has an advantage that detection efficiency is good and sensitivity can be further improved. The radioactive isotope is not particularly limited, and a radioactive isotope that is usually used for measuring the target substance amount can be used. Specifically, examples thereof include radio isotopes such as $^{125}I$, $^{32}P$, $^{14}C$, $^{35}S$ and $^{3}H$. The enzyme is not particularly limited, and an enzyme that is usually used for measuring the target substance amount can be used. Specifically, examples thereof include alkaline phosphatase, peroxydase (for example, horseradish peroxidase), β-galactosidase, and phycoerythrin. The redox substance is not particularly limited, and a redox substance that is usually used for measuring the target substance amount can be used. Specifically, the redox substance is a compound containing redox metal ions selected from iron, vanadium, chromium, zinc, and mixtures thereof. More specifically, examples thereof include ferrocene, 1,1'-dimethylferrocene, ferrocyanide and ferrocyanide, ruthenium (III) and ruthenium (II) hexaamine, fendinmethsulfate (PMS), and m-PMS.

The method of fixing the second receptor to the labeled substance is also not particularly limited, and is the same as that described in the magnetic particles (first receptor-fixed magnetic particles) according to this disclosure. Therefore, the description thereof is omitted here. In the description of the "method of fixing the first receptor to the magnetic particles" in the above (Magnetic Particles to which First Receptor that Specifically Recognizes Site of Target Substance is Fixed), the "magnetic bead" or the "magnetic particles" can be applied to replace the "labeled substance."

A usage amount of the second receptor-fixed labeled substance according to this disclosure is not particularly limited and is appropriately selected in accordance with the target substance amount, whereas the usage amount is usually larger than the target substance amount. For example, when one target substance binds to the labeled substance (for example, in a labeled substance to which a reducing antibody is fixed), the usage amount of the second receptor-fixed labeled substance according to this disclosure is an amount such that preferably 1 mol to 100 mol, more preferably more than 1 mol and less than 50 mol, and particularly preferably 2 mol to 50 mol of the second receptor (for example, an antibody) is present with respect to 1 mol of the target substance. When two target substances bind to the labeled substance (for example, in a labeled substance to which an IgG antibody is fixed), the amount of the second receptor-fixed labeled substance is twice the above-described preferred amount. The labeled substance amount can be predicted to some extent by those skilled in the art, such as an insulin amount contained in blood, and an upper limit of a predicted range is set as the labeled substance amount. When the labeled substance amount cannot be predicted by those skilled in the art, an excess amount of the second receptor-fixed labeled substance (for example, an amount such that 0.1 µg/mL to 100 µg/mL of the second receptor-fixed labeled substance or 1 nM to 100 nM of the second receptor (for example, an antibody) is contained in the reaction solution) may be used.

A mixing ratio of the labeled substance (second receptor-fixed labeled substance) according to this disclosure to the magnetic particles (first receptor-fixed magnetic particles) according to this disclosure is not particularly limited, whereas it is preferable that the first receptor-fixed magnetic particles are present in a larger amount than that of the second receptor-fixed labeled substance. Accordingly, it is possible to more efficiently capture the labeled substance present in the sample while more effectively preventing the decrease in sensitivity due to the unreacted labeled substance. Specifically, when one target substance binds to both the labeled substance and the magnetic particles (for example, in magnetic particles or a labeled substance to which a reducing antibody is fixed), a mixing ratio of the labeled substance (second receptor-fixed labeled substance) according to this disclosure to the magnetic particles (first receptor-fixed magnetic particles) according to this disclosure is a ratio such that the first receptor bound to the magnetic particles according to this disclosure is preferably present in an amount of more than 1 mol and 10,000 mol or less, more preferably 10 mol to 1000 mol, and particularly preferably more than 10 mol and 50 mol or less with respect to 1 mol of the second receptor bound to the labeled substance according to this disclosure. With such a mixing ratio, it is possible to more efficiently capture the labeled substance present in the sample while more effectively preventing the decrease in sensitivity due to the unreacted labeled substance.

(Formation of Target Substance-Magnetic Particle-Labeled Substance Complex)

By mixing the sample containing the target substance with the magnetic particles (first receptor-fixed magnetic particles) according to this disclosure and the labeled substance (second receptor-fixed labeled substance) according to this disclosure, the target substance and the magnetic particles are bound to each other via the first receptor, and the target substance and the labeled substance are bound to each other via the second receptor, thereby forming a target substance-magnetic particle-labeled substance complex. A formation condition of the target substance-magnetic particle-labeled substance complex at this time is not particularly limited as long as the desired complex is formed. For example, the sample containing the target substance, the first receptor-fixed magnetic particles, and the second receptor-fixed labeled substance are mixed in a buffer solution. Here, the buffer solution is not particularly limited, and a known buffer solution can be used. Specifically, examples thereof include a buffer solution similar to that exemplified in the above section (Formation of Target Substance-Magnetic Particle Complex). The pH of the buffer solution is not particularly limited as long as the receptor maintains the target substance binding activity. However, in consideration of preventing the decrease in target substance binding activity of the receptor, the pH is usually preferably near neutral to weakly basic. From such a viewpoint, the pH of the buffer solution is more preferably 6.0 to 9.0, and particularly preferably 6.0 to 8.0. The mixing temperature is preferably from 4° C.; to 40° C., and more preferably from 25° C.; to 37° C. The mixing time is preferably 1 to 60 minutes, and more preferably 5 to 30 minutes.

By mixing (reacting) the sample containing the target substance, the magnetic particles (first receptor-fixed magnetic particles) according to this disclosure, and the labeled substance (second receptor-fixed labeled substance) according to this disclosure, a mixture containing the target substance-magnetic particle-labeled substance complex is obtained. Specifically, the above mixture contains a target substance-magnetic particle-labeled substance complex in which the magnetic particles and the labeled substance are bound via the target substance, a target substance-magnetic particle complex in which the target substance is bound only to magnetic particles, a target substance-labeled substance complex in which the target substance is bound only to the labeled substance, unreacted magnetic particles, and unreacted labeled substances.

(Separation of Target Substance-Magnetic Particle-Labeled Substance Complex)

The mixture containing the target substance-magnetic particle-labeled substance complex thus formed is subjected to electrophoresis, and the target substance-magnetic particle-labeled substance complex is separated by magnetism during electrophoresis. That is, during electrophoresis or before electrophoresis, the magnetic particles present in the target substance-magnetic particle-labeled substance complex are captured by magnetism, and the target substance (target substance-magnetic particle-labeled substance complex) of interest is recovered. The target substance-magnetic particle-labeled substance complex may be in a form of being contained in a buffer solution as obtained in the above (Formation of Target Substance-Magnetic Particle-Labeled Substance Complex), or may be in a form of being separated from a buffer solution, or may be in a form of being separated from a buffer solution and then dispersed in another buffer solution. Here, electrophoresis is not particularly limited, and known electrophoresis can be used. Specifically, since the electrophoresis is the same as that described in the above section (Separation of Target Substance-Magnetic Particle Complex), the description thereof is omitted here.

During the electrophoresis, the target substance-magnetic particle-labeled substance complex of interest is separated by magnetism. Specifically, the target substance-magnetic particle-labeled substance complex, the target substance-magnetic particle complex in which the target substance is bound only to the magnetic particles, and the unreacted magnetic particles are captured by magnetism. Therefore, during the electrophoresis, components other than the target substance contained in the sample, a reagent diluent (for example, a buffer solution, when used), a substance to which the target substance is non-specifically bound (such as a target substance-labeled substance complex in which the target substance is bound only to the labeled substance), and the unreacted labeled substance are separated.

In this disclosure, the magnet is installed during electrophoresis. Here, since the specific description of the magnet is the same as that described in the above section (Separation of Target Substance-Magnetic Particle Complex), the description thereof is omitted here.

(Detection of Signal Intensity of Target Substance-Magnetic Particle-Labeled Substance Complex)

A target substance amount of interest is measured by detecting signal intensity of the target substance-magnetic particle-labeled substance complex separated as above. In the above separation step, in addition to the target substance-magnetic particle-labeled substance complex, the target substance-magnetic particle complex in which the target substance is non-specifically bound only to the magnetic particles and the unreacted magnetic particles are also captured by the magnet. In the present embodiment, an antibody that specifically binds to the target substance is used as the labeled substance. Therefore, since no target substance is present in the unreacted magnetic particles, the labeled substance does not bind to the unreacted magnetic particles. That is, the unreacted magnetic particles have no substantial influence on the signal intensity (hence, measurement accuracy) of the target substance-magnetic particle-labeled substance complex. Therefore, in this step, the signal intensity of the target substance is selectively detected, that is, the target substance amount can be measured with high accuracy. In addition, other components (for example, blood cells) in the sample that cause the decrease in sensitivity and the unreacted labeled substance are moved from the magnet to the cathode or anode side by electrophoresis. A blending amount of the labeled substance is such that the target substance can be sufficiently detected in a measurement target range in consideration of the type of the target substance, the usage amount of other reagent components such as magnetic particles, and the type of the sample. Hence, according to the method of this disclosure, the amount of the target substance of interest can be measured with high sensitivity (high accuracy).

Hereinafter, an embodiment in which the signal intensity of the complex is detected after performing the separation of the target substance-magnetic particle-labeled substance complex by carrier-free electrophoresis and magnetism will be described with reference to the drawings. This disclosure is not limited to the following embodiment.

FIGS. 1A to 1D are diagrams illustrating steps of a method according to this disclosure.

In the description of FIGS. 1A, B, and C, the description of matters repeated with the description in the first embodiment of this disclosure will be omitted here.

First, as shown in FIG. 1A, the electrophoretic base material (for example, a capillary) 5 is filled with the reagent 4 containing the first receptor-fixed magnetic particles and the second receptor-fixed labeled substance. The electrophoretic base material 5 is arranged on the substrate 6 of an electrophoresis device. The electrodes (for example, platinum electrodes) 2 and 3 are provided at both ends of the electrophoretic base material 5. Accordingly, an electric field is applied in the longitudinal direction of the electrophoretic base material 5. The reagent may contain any one of the first receptor-fixed magnetic particles and the second receptor-fixed labeled substance. In addition to the first receptor-fixed magnetic particles and the second receptor-fixed labeled substance, the reagent may contain pH adjusting agents (for example, sodium hydroxide, sodium carbonate, sodium hydrogen carbonate, sulfuric acid, hydrochloric acid, and phosphoric acid), buffering agents (for example, sodium hydrogen phosphate, sodium phosphate, and Tris-HCL), hemolytic agents such as saponin, and surfactants.

An amount of the first receptor-fixed magnetic particles in the reagent is not particularly limited, and the same amount as described in the above section (Magnetic Particles to which First Receptor that Specifically Recognizes Site of Target Substance is Fixed) can be used. Similarly, an amount of the second receptor-fixed labeled substance and a mixing ratio of the first receptor-fixed magnetic particles to the second receptor-fixed labeled substance are not particularly limited, and the same amount and the ratio as described in the above section (Labeled Substance to which Second Receptor that Specifically Recognizes Site Different From Site of Target Substance is Fixed) can be used.

In the present embodiment, the electrophoretic base material 5 is filled with the reagent containing the first receptor-fixed magnetic particles and the second receptor-fixed labeled substance in advance. Alternatively, after the first receptor-fixed magnetic particles and the second receptor-fixed labeled substance and the target substance (sample) may be reacted in advance to form the target substance-magnetic particle-labeled substance complex, the electrophoretic base material 5 may be filled with a reaction product thereof (second' embodiment). In the case of the second' embodiment, it is preferable to separately provide a chamber (not shown) for the above reaction on the substrate 6.

Alternatively, in another embodiment, a reagent solution containing the first receptor-fixed magnetic particles, the second receptor-fixed labeled substance, and a buffer may be dropped onto both end portions of the electrophoretic base material to form a liquid pool, the electrophoretic base material may be filled with the reagent solution by the capillarity action, the electrodes (for example, platinum electrodes) 2 and 3 may be installed at both ends of the electrophoretic base material, and a sample containing the target substance may be dropped onto any one of the electrodes (third' embodiment).

Next, as shown in FIG. 1B, the magnet 8 is installed on the platinum electrode 2 (anode) side of the electrophoretic base material 5. Accordingly, the magnetic particles contained in the target substance-magnetic particle complex are captured by the magnet 8. Next, as shown in FIG. 1C, after the magnet 8 is moved in the longitudinal direction of the electrophoretic base material 5, electrophoresis is started. Accordingly, the target substance-magnetic particle-labeled substance complex can be selectively separated. Therefore, in the detection of the signal intensity described in detail below, the amount of the target substance-magnetic particle-labeled substance complex (hence, the labeled substance contained in the complex) can be measured with high accuracy. That is, according to a preferred embodiment of the present disclosure, after obtaining a mixture containing the target substance-magnetic particle-labeled substance complex, the target substance-magnetic particle-labeled substance complex is collected at a predetermined position by magnetism and then subjected to electrophoresis, whereby the target substance-magnetic particle-labeled substance complex and the unreacted second receptor-fixed labeled substance (second receptor-fixed labeled substance that does not bind to the target substance) are separated from each other. Here, although a movement position of the magnet 8 is not particularly limited, it is preferable to set the magnet at a position similar to that described in the above section (Separation of Target Substance-Magnetic Particle Complex) in FIG. 1C.

The magnet 8 is moved along the electrophoretic base material 5 at least once between the cathode and the anode on an outer surface of the electrophoretic base material 5 and at a position close to an outer surface of the electrophoretic base material 5. Thereafter, the magnet 8 is arranged at the predetermined position to start the electrophoresis. The arrangement position of the magnet 8 is not particularly limited, and may be any position as long as an appropriate magnetic force can be applied to the electrophoretic base material 5, and the magnet can be arranged at the position similar to that specified in the above section (Separation of Target Substance-Magnetic Particle Complex).

As described above, the sample immediately before electrophoresis (hereinafter, also referred to as "specimen 2") contains the target substance-magnetic particle-labeled substance complex, the target substance-magnetic particle complex, the target substance-labeled substance complex, the unreacted magnetic particles, and the unreacted labeled substance in addition to the components contained in the sample (for example, a living-body-derived component such as blood cells) and the components contained in the buffer solution. In the above electrophoresis, the target substance-magnetic particle-labeled substance complex, the target substance-magnetic particle complex, and the unreacted magnetic particles are captured by the magnet. However, by appropriately adjusting the mixing ratio of the labeled substance to the magnetic particles, a mixing amount of the target substance-magnetic particle complex can be minimized. Therefore, the target substance-magnetic particle-labeled substance complex and the unreacted magnetic particles are selectively captured by the magnet. However, the labeled substance does not specifically bind to the unreacted magnetic particles (not detected in the detection of the signal intensity below). Therefore, by measuring the signal intensity of a separated product after electrophoresis, the amount of the target substance-magnetic particle-labeled substance complex (hence, the target substance) can be measured with high sensitivity (high accuracy).

Figure 1D:
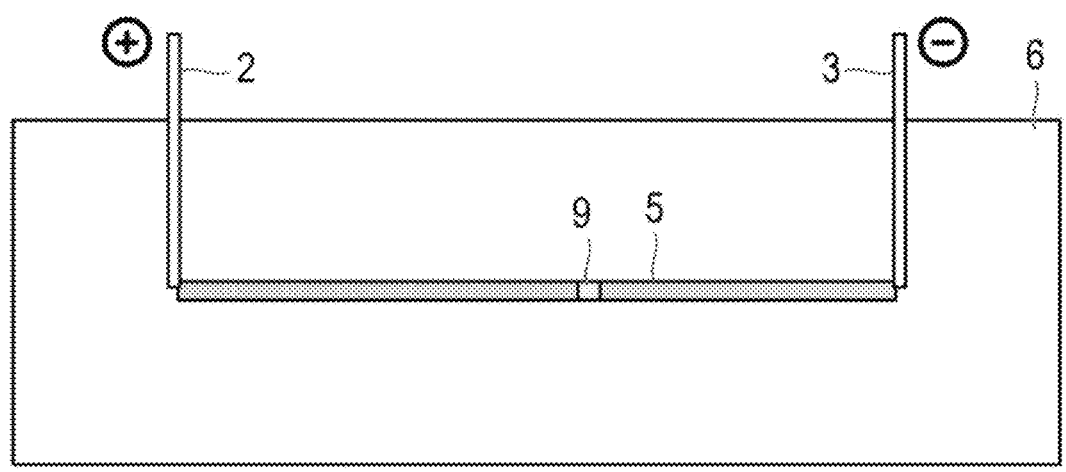

Next, as shown in FIG. 1D, the signal intensity of a target substance-magnetic particle-labeled substance complex 9 present in the electrophoretic base material 5 on which the magnet 8 is arranged is detected. Here, the signal intensity of the labeled substance present in the complex corresponds to the target substance amount. That is, a calibration curve with respect to the target substance amount can be created for the signal intensity of a band of a target substance-magnetic particles-labeled substance measured in advance. By comparing the detected signal intensity of a band of the target substance-magnetic particle-labeled substance complex based on the calibration curve, the target substance amount in the sample can be measured accurately. That is, according to a preferred embodiment of this disclosure, the calibration curve of the signal intensity of the target substance-magnetic particle-labeled substance complex with respect to the target substance amount is created using a target substance whose amount is known in advance, and the target substance amount in the sample is measured based on the calibration curve and the detected signal intensity of the target substance-magnetic particle-labeled substance complex.

In this disclosure, it is preferable to create a relationship (calibration curve) regarding the signal intensity of the band of the target substance-magnetic particle-labeled substance complex with respect to the target substance amount using a sample whose target substance amount is known in advance. That is, the sample whose target substance amount is known in advance is subjected to the same operation as above, the signal intensity of the band of the target substance-magnetic particle-labeled substance complex is calculated, and the calibration curve regarding a standard substance amount and the signal intensity of the band is created. Here, as a measurement method for the signal intensity, a known method can be used in accordance with the type of the labeled substance. For example, when the labeled substance is a fluorescent substance, fluorescence intensity is measured with a fluorescence measurement device (fluorescence scanner) or an image processing system in the case of performing quantification. When the labeled substance is a radioactive isotope, a radiation amount is measured with a radiation counting device. When the labeled substance is an enzyme, detection and/or quantification of a product produced by the enzyme can be performed by measuring absorbance of the product. For example, when 3,3',5,5'-tetramethylbenzidine is used as an enzyme substrate, the absorbance at 655 nm may be measured. When the labeled substance is a redox substance, a generated electrochemical signal is measured.

For the quantification of the target substance, for example, the target substance amount contained in the sample is easily obtained by creating the calibration curve using the fluorescence intensity obtained by using the standard sample containing the target substance having a known concentration.

The calibration curve obtained by this disclosure is an effective calibration curve because it is a constant calibration curve regardless of external factors such as an electrophoresis condition. Therefore, by using the calibration curve, the target substance amount in the sample can be accurately measured.

The above detection method is a very useful assay method in clinical tests, especially when the target substance is a marker related to some disease.

Although the magnet is removed in FIG. 1D, in order to prevent the diffusion of the target substance (target substance-magnetic particle-labeled substance complex), it is preferable to appropriately detect the signal intensity while the magnet remains arranged on the electrophoretic base material 5 (for example, from below the substrate). From this viewpoint, it is preferable that the substrate and the electrophoretic base material are transparent.

[Diagnosis Method]

A third embodiment of this disclosure relates to a diagnosis method for a target-substance-related disease using the separation and measurement method according to the first or second embodiment. Specifically, the diagnosis method for a target-substance-related disease includes: collecting a sample from a subject; mixing a target substance in the sample, magnetic particles to which a first receptor that specifically recognizes a site of the target substance is fixed, and a labeled substance to which a second receptor that specifically recognizes a site different from the site of the target substance is fixed to obtain a mixture containing a target substance-magnetic particle-labeled substance complex; performing electrophoresis on the mixture; separating the target substance-magnetic particle-labeled substance complex by magnetism and electrophoresis; then detecting signal intensity of the target substance-magnetic particle-labeled substance complex; and determining whether the subject has a disease related to the target substance by comparing the signal intensity to a value of the target substance in a healthy subject. Therefore, this disclosure provides a diagnosis method for a a target-substance-related disease including: collecting a sample from a subject, mixing a target substance in the sample, magnetic particles to which a first receptor that specifically recognizes a site of the target substance is fixed, and a labeled substance to which a second receptor that specifically recognizes a site different from the site that is recognized by the target substance is fixed to obtain a mixture containing a target substance-magnetic particle-labeled substance complex, separating the target substance-magnetic particle-labeled substance complex by magnetism and electrophoresis, and then detecting signal intensity (signal intensity 1) of the target substance-magnetic particle-labeled substance complex; collecting a sample from a healthy subject, mixing a target substance in the sample, the magnetic particles to which the first receptor that specifically recognizes the site of the target substance is fixed, and the labeled substance to which the second receptor that specifically recognizes the site different from the site of the target substance is fixed to obtain a mixture containing a target substance-magnetic particle-labeled substance complex, separating the target substance-magnetic particle-labeled substance complex by magnetism and electrophoresis, and then detecting signal intensity (signal intensity 2) of the target substance-magnetic particle-labeled substance complex; and comparing the signal intensity 1 with the signal intensity 2 to determine whether the subject has a disease related to the target substance. Here, the subject or the healthy subject is preferably human or a mammal other than human. When the target substance is insulin, examples of the above-described disease include insulinoma, obesity, liver disease, Cushing's syndrome, acromegaly, abnormal insulinemia, insulin autoimmune syndrome, diabetes, hypoglycemia, hyponutrition, pheochromocytoma, and pituitary adrenal hypofunction. If the signal intensity of the subject is higher than the value of the healthy subject, the subject may suffer from the above-described diseases such as insulinnorma, obesity, liver disease, Cushing's syndrome, acromegaly, abnormal insulinemia, and insulin autoimmune syndrome. On the other hand, if the signal intensity of the subject is lower than the value of the healthy subject, the subject may suffer from diabetes, hypoglycemia, hyponutrition, pheochromocytoma, and pituitary adrenal hypofunction. That is, when the target substance is insulin and the signal intensity 1 is lower than the signal intensity 2, it is determined that the subject suffers from or has a risk of suffering from diabetes, hypoglycemia, hyponutrition, pheochromocytoma or pituitary adrenal hypofunction.

[Inspection Kit or Inspection System]

A fourth embodiment of this disclosure relates to an inspection kit for a target-substance-related disease, which includes magnetic particles to which a first receptor that specifically recognizes a site of a target substance is fixed (first receptor-fixed magnetic particles), a labeled substance to which a second receptor that specifically recognizes a site different from the site of the target substance is fixed (second receptor-fixed labeled substance), and a magnet. Therefore, this disclosure provides an inspection kit for a target-substance-related disease, which includes magnetic particles to which a first receptor that specifically recognizes a site of the target substance is fixed, a labeled substance to which a second receptor that specifically recognizes a site different from the site that is recognized by the target substance is fixed, and a magnet.

A fifth embodiment of this disclosure relates to an inspection system for a target-substance-related disease, which includes magnetic particles to which a first receptor that specifically recognizes a site of the target substance is fixed, a labeled substance to which a second receptor that specifically recognizes a site different from the site of the target substance is fixed, a magnet, and an electrophoresis device (preferably a carrier-free electrophoresis device). Therefore, this disclosure provides an inspection system for a target-substance-related disease, which includes magnetic particles to which a first receptor that specifically recognizes a site of the target substance is fixed, a labeled substance to which a second receptor that specifically recognizes a site different from the site that is recognized by the target substance is fixed, a magnet, and an electrophoresis device. In the present embodiment, it is preferable that the electrophoresis device is a carrier-free electrophoresis device.

The first receptor-fixed magnetic particles and the second receptor-fixed labeled substance stored in the inspection kit may be contained in one or separate containers. The first receptor-fixed magnetic particles and the second receptor-fixed labeled substance may be contained in a container together with a buffer solution. The inspection kit may be an electrophoresis set containing a buffer solution for assay or a concentrated stock solution thereof. That is, a six embodiment of this disclosure relates to an inspection system for a target-substance-related disease, which includes magnetic particles to which a first receptor that specifically recognizes a site of the target substance is fixed, a labeled substance to which a second receptor that specifically recognizes a site different from the site of the target substance is fixed, a magnet, and an electrophoresis set (preferably a carrier-free electrophoresis set). Therefore, this disclosure provides an inspection system for a target-substance-related disease, which includes magnetic particles to which a first receptor that specifically recognizes a site of the target substance is fixed, a labeled substance to which a second receptor that specifically recognizes a site different from the site that is recognized by the target substance is fixed, a magnet, and an electrophoresis set. In the present embodiment, it is preferable that the electrophoresis set is a carrier-free electrophoresis set. Here, the electrophoresis set can additionally include general electrophoresis instruments such as an electrophoresis tank, a glass plate for electrophoresis, a buffer tank, a spacer, a comb, a clip, a power supply, or a perista pump; electrophoretic reagents; and detection reagents.

The inspection kit or the inspection system according to the present embodiment may further include a standard sample having a known amount (concentration) and a container containing the same in the kit or system. Each reagent stored in the inspection kit or the inspection system may be dispensed and provided in a container for each sample measurement, or may be provided in an individual container in which a plurality of sample measurements are collected for each reagent. In the latter case, each reagent is dispensed into a predetermined measurement container during use. When the reagent is provided for each sample measurement, the container containing each reagent may be integrally formed as a cartridge, or each reagent may be stored in a different section of the cartridge. When the first receptor-fixed magnetic particles or the second receptor-fixed labeled substance is stored in the kit in a solid form, the inspection kit or the inspection system may further stores a buffer solution as described above for forming the complex. The container, which may be included in the inspection kit or the inspection system, does not interact with the first receptor-fixed magnetic particles or the second receptor-fixed labeled substance, and any material that does not interfere with the reaction used in the assay, such as an enzymatic reaction or a chemical luminescence reaction, may be used. If necessary, the surface may be pre-treated and provided so as not to cause such an interaction. A general instruction manual is attached to the inspection kit or the inspection system.

EXAMPLES

Effects of this disclosure will be described with reference to the following Examples and Comparative Examples. However, the technical scope of this disclosure is not limited to the following Examples. In the following Examples, unless otherwise specified, the operation was performed at room temperature (25° C.). Unless otherwise specified, "%" and "parts" mean "% by mass" and "parts by mass", respectively.

Example 1

(Preparation of First Receptor-Fixed Magnetic Particles)

Mouse anti-human fatty acid binding protein (H-FABP) IgG monoclonal antibody 28 (Monoclonal mouse anti-human fatty acid binding protein (FABP) 28, manufactured by Hytest Ltd.) in an amount of 0.032 mL (0.2 mg) was biotinylated according to a protocol of the manufacturer using Biotin Labeling Kit-SH (manufactured by Dojin Chemical Laboratories), to obtain 0.2 mL (1 mg/mL) of a PBS solution (pH: 7.4) (solution A-1) containing Biotin-labeled Anti H-FABP (28) (biotinylated H-FABP antibody).

To 0.2 mL of the solution A-1, 0.2 mL of Magnosphere MS300/Streptavidin (average particle size: 3.0 μm, manufactured by JSR Life Sciences Corporation) (magnetic particles, magnetic particle amount: 2 mg) was added, and a biotin part of the biotinylated FABP antibody was reacted with the streptavidin part of the magnetic particles at 4° C.; overnight, to obtain a reaction solution (solution A-2) containing a Biotin-labeled Anti H-FABP (28)/Streptavidin magnetic bead complex (first receptor-fixed magnetic particles). After incubation for a predetermined time, the first receptor-fixed magnetic particles were separated from the reaction solution (solution A-2) using a permanent magnet and washed with PBS (pH: 7.4) containing 0.10 of BSA. After final washing, the first receptor-fixed magnetic particles were isolated by decantation, then 0.2 mL of PBS (pH: 7.4) containing 0.1% of BSA was added to prepare a first receptor-fixed magnetic particle solution (solution A-3). Concentrations of the first receptor-fixed magnetic particles, the antibody and the magnetic particles in the solution A-3 were 11 mg/mL, 1 mg/mL and 10 mg/mL, respectively.

(Preparation of Second Receptor-Fixed Labeled Substance)

To 0.3 mL of a 0.1 M phosphate buffer (pH: 6.0) containing 50 mM EDTA, 0.055 mL (0.3 mg) of mouse anti-human fatty acid binding protein (FABP) IgG monoclonal antibody 25 (Monoclonal mouse anti-human fatty acid binding protein (FABP) 25, manufactured by Hytest Ltd.) was added, to prepare an antibody solution (solution B-1). To this antibody solution (solution B-1), 0.05 mL of a 0.1 M phosphate buffer (pH: 6.0) containing 0.1 M mercaptoethylamine hydrochloride and 50 mM EDTA was added. The obtained solution was incubated at 37° C.; for 2 hours to reduce a disulfide bond of the antibody to form a sulfhydryl group (—SH), so as to obtain a solution containing a reducing antibody (solution B-2). The solution (solution B-2) was desalted to obtain 0.4 mL of a PBS solution (solution B-3) containing the reducing antibody.

Separately, 0.5 mL of IRDye (registered trademark) 800CW Maleimide (manufactured by LI-COR Biosciences) (labeled substance) (excitation wavelength: 800 nm) was dissolved by adding 0.03 mL of N,N-dimethylformamide (DMF), to obtain a labeled substance solution (solution B-4). To 0.4 mL of the PBS solution (solution B-3) containing the reducing antibody, 0.01 mL of the labeled substance solution (solution B-4) was added, and the mixture was incubated at 37° C.; for 30 minutes to react the sulfhydryl group (—SH) of the reducing antibody with the maleimide group of the labeled substance, to obtain a reaction solution (solution B-5) containing the IRDye800CW-labeled AntiH-FABP (25) complex (second receptor-fixed labeled substance). After incubating for a predetermined time, the reaction solution (solution B-5) thus obtained was buffer-exchanged with PBS using Zeba spin desalting column (Zeba™ Spin Desalting Columns, 7K MWCO, 0.5, manufactured by Thermo Fisher Scientific Co., Ltd.), to obtain 0.4 mL of a PBS solution (solution B-6) containing the second receptor-fixed labeled substance. The buffer exchange was performed by dividing the solution into 0.2 mL portions using two spin desalting columns, and then combining the solution with a column treatment solution (solution B-6).

Finally, the solution B-6 thus obtained was diluted with PBS (pH: 7.4) containing 0.1% BSA such that the antibody concentration was 0.1 mg/mL, to prepare a second receptor-fixed labeled substance solution (solution B-7).

(Preparation of H-FABP Solution)

Into 0.1 mg of human fatty acid binding protein (H-FABP) (Fatty acid binding protein (FABP), human, manufactured by Hytest Ltd.), 2 mL of a PBS solution containing 0.1% BSA was added and dissolved, to prepare an H-FABP solution (H-FABP concentration: 0.05 mg/mL).

(Preparation of Electrophoresis Solution)

The first receptor-fixed magnetic particle solution (solution A-3), the second receptor-fixed labeled substance solution (solution B-7), and the H-FABP solution as prepared above, PBS (pH: 7.4) containing 0.1% BSA ("0.1% BSA PBS" in Table 1 below), and 0.1 M Tris-HCl (pH 8.5) ("Tris-HCl" in Table 1 below) were mixed and reacted at 25° C.; for 5 minutes so as to have a composition (pH: 8.5) shown in Table 1 below, to prepare electrophoresis solutions 1 to 5 (samples 1 to 5) containing fatty acid-binding protein-Biotin-labeled Anti H-FABP (28)/Streptavidin magnetic bead-IRDye800CW-labeled Anti H-FABP (25) complexes 1 to 5 (complexes 1 to 5). In Table 1 below, a "dilution rate of H-FABP solution" indicates a dilution ratio when the H-FABP solution prepared above is diluted, and an "H-FABP solution after dilution" indicates the amount of the H-FABP solution added after being diluted at the above-described predetermined dilution rate. Therefore, for example, the sample 1 means that 1 μL of the H-FABP solution prepared above was diluted twice. In Table 1 below, "antibody/H-FABP (molar ratio) in solution A-3" means a molar ratio of Anti H-FABP (28) (first receptor) to fatty acid binding protein (H-FABP, target substance) in each sample. Similarly, "antibody/H-FABP (molar ratio) in solution B-7" means a molar ratio of Anti H-FABP (25) (second receptor) to fatty acid binding protein (H-FABP, target substance) in each sample. An amount of the biotin bound to the magnetic particles can be calculated based on an amount described in the instruction manual of the magnetic particles used. In addition, the antibody and the biotin have a molar ratio of 1:1 and can be calculated assuming that the antibody and the biotin are all bound to each other.

TABLE 1

Composition of Electrophoresis Solution

| | Sample 1 | Sample 2 | Sample 3 | Sample 4 | Sample 5 |
|---|---|---|---|---|---|
| Final concentration of H-FABP | 9.2 nM (138 ng/ml) | 4.6 nM (69 ng/ml) | 1.1 nM (17 ng/mL) | 0.6 nM (9 ng/mL) | 0 nM (0 ng/ml) |
| Solution A-3 (μL) | 10 | 10 | 10 | 10 | 10 |
| Solution B-7 (μL) | 6 | 6 | 6 | 6 | 6 |
| Dilution rate (times) of H-FABP solution | 2 | 16 | 16 | 64 | — |
| H-FABP solution (μL) after dilution | 1 | 4 | 1 | 2 | 0 |
| 0.1% BSA PBS (μL) | 3 | 0 | 3 | 2 | 4 |
| Tris-HCl (μL) | 160 | 160 | 160 | 160 | 160 |
| Antibody/H-FABP (molar ratio) in solution A-3 | 30.2 | 60.4 | 252.5 | 463.0 | — |
| Antibody/H-FABP (molar ratio) in solution B-7 | 2.2 | 4.3 | 18.2 | 33.3 | — |

(Preparation of Electrophoretic Solution Filled Glass Square Tube)

Figure 2A:
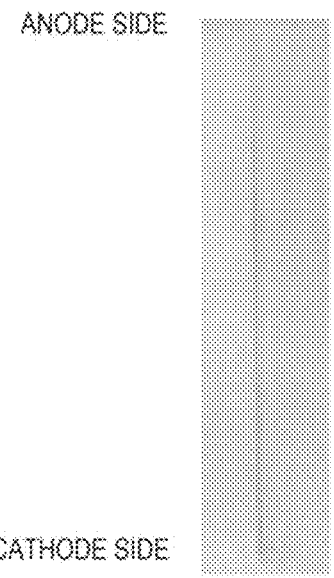
FIG. 2A is a photograph of a glass square tube before magnetic recovery according to Examples (Preparation of Electrophoretic Solution Filled Glass Square Tube).
Figure 2B:
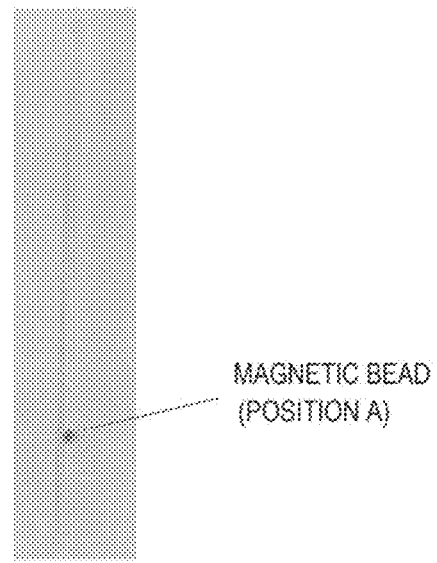
FIG. 2B is a photograph of the glass square tube after the magnetic recovery according to an Example (Preparation of Electrophoretic Solution Filled Glass Square Tube).

A glass square tube (outer side: 1.5 mm, inner side: 1.0 mm, wall thickness: 0.25 mm, length: 40 mm, material: quartz) (FIG. 2A) was filled with 0.04 mL of each of the samples 1 to 5 prepared as the above (Preparation of Electrophoresis Solution). A neodymium permanent magnet was slid over the tube filled with each sample along an extending direction of the tube and the complexes 1 to 5 and the unreacted first receptor-fixed magnetic particles were collected at one place (position A) to obtain glass square tubes 1 to 5 (FIG. 2B). The magnet was installed at a point where a ratio (Y/X) of a distance (Y) from the cathode to the magnet to a distance (X) from the cathode to the anode was 1/5.

(Electrophoresis)

Figure 3:
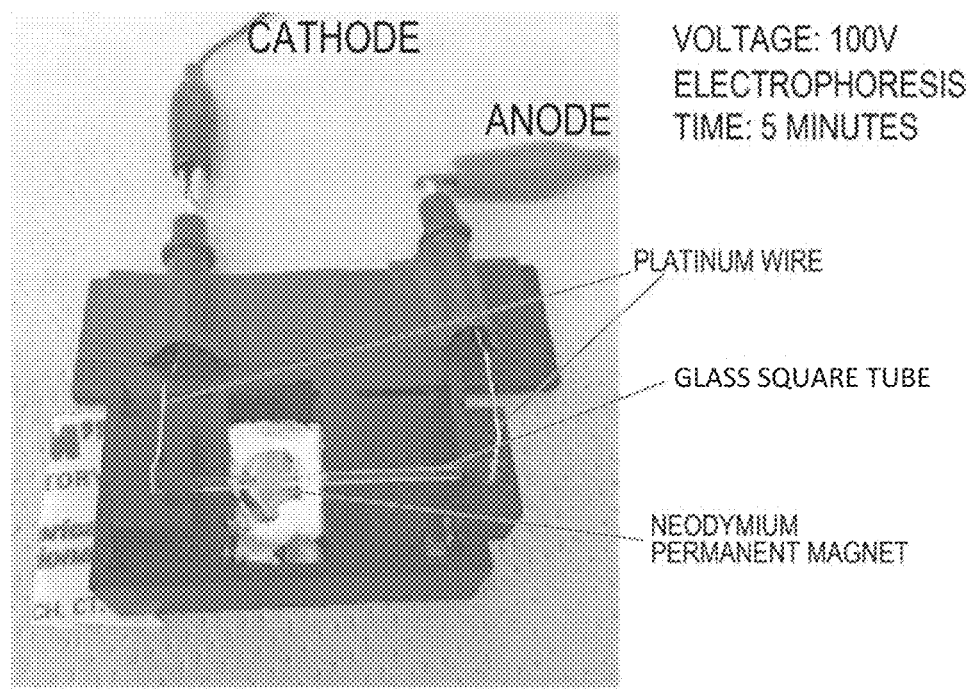

After setting each of the glass square tubes 1 to 5 prepared in the above (Preparation of Electrophoresis Solution) in the electrophoresis device shown in FIG. 3, electrophoresis was performed at a voltage of 100 V for 5 minutes.

Figure 4:
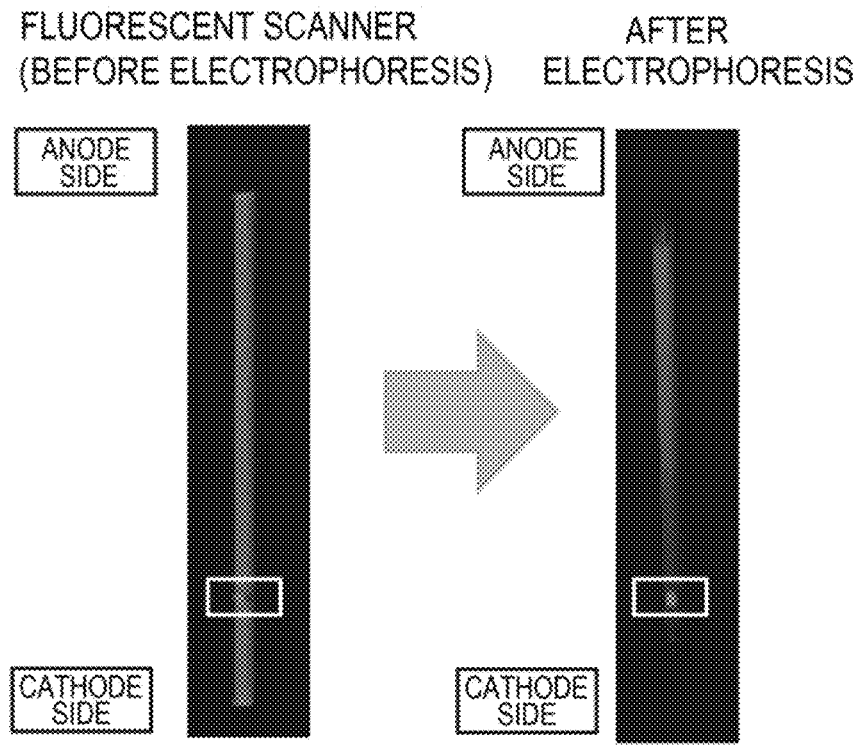
FIG. 4 is a photograph of the glass square tube when measured by a fluorescent scanner before and after electrophoresis in the Examples (Electrophoresis).

After electrophoresis, the glass square tubes 1 to 5 were removed from the electrophoresis device while fixing the neodymium permanent magnet at the position A such that the complex in each tube did not move. Fluorescence intensities at the position A of the glass square tubes 1 to 5 were measured using a fluorescence scanner (Odyssey CLx imaging system, manufactured by LI-COR Biosciences). FIG. 4 shows photographs of the glass square tube filled with the sample 1 as measured by the fluorescence scanner before and after electrophoresis. In FIG. 4, a portion surrounded by a white square indicates a place where the complex is present. From FIG. 4, it can be seen that the complex 1 can be well separated from the unreacted second receptor-fixed labeled substance (without binding of fatty acid-binding protein) after electrophoresis.

Figure 5:
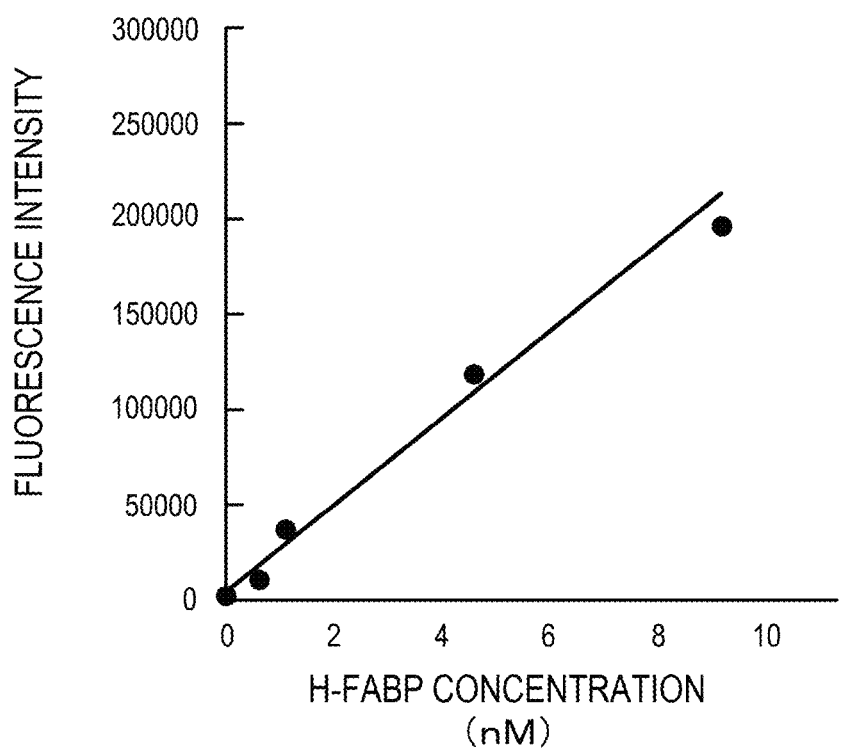
FIG. 5 is a graph illustrating a relationship of fluorescence intensity with respect to a final concentration of H-FABP in the Examples.

The fluorescence intensity with respect to the final concentration of H-FABP was plotted. The result is shown in FIG. 5. From FIG. 5, in a H-FABP concentration range of 0 nM to 9.2 nM (138 ng/mL), a good positive correlation (linearity) (y=21384x+7190 (Here, y represents the signal intensity (fluorescence intensity) and x represents the H-FABP concentration (nM)), $R^2$=0.9867) is observed between the signal intensity (fluorescence intensity) of the target substance-magnetic particle-labeled substance complex and the H-FABP concentration. Therefore, it is expected that the amount of the fatty acid-binding protein in the sample can be measured with high accuracy based on a calibration curve prepared using a target substance whose amount is known in advance. Although experiments have been conducted using a fatty acid-binding protein in the Examples, it is considered that similar results can be obtained for other receptors such as an insulin antibody and an insulin receptor. Although the fatty acid-binding protein has been used in the Examples, a living-body-derived component other than the complex moves to the anode side by electrophoresis even when a biological sample such as blood is used. Therefore, even in such a case, it is considered that the complex can be well separated from other biological components.

REFERENCE NUMERAL LIST 2, 3 electrode
4 reagent
5 electrophoretic base material
6 substrate
7 sample containing target substance
8 magnet
9 target substance-magnetic particle-labeled substance complex

The invention claimed is:

1. A method for measuring a target substance amount, the method comprising:
    forming a mixture containing:
        a target substance-magnetic particle-labeled substance complex that comprises:
            a biological sample containing a target substance, and
            magnetic particles to which a first receptor is fixed, wherein the first receptor is adapted to specifically recognize a site of the target substance, and
        a labeled substance to which a second receptor is fixed, wherein the second receptor is adapted to specifically recognize a site different from the site of the target substance;
    separating the target substance-magnetic particle-labeled substance complex from the mixture by magnetism and electrophoresis; and
    a subsequently, measuring the target substance amount in the biological sample, which comprises detecting a signal intensity of the target substance-magnetic particle-labeled substance complex.

2. The method according to claim 1,
wherein the step of separating the target substance-magnetic particle complex from the mixture comprises:
collecting the target substance-magnetic particle complex at a predetermined position by magnetism, and subsequently, subjecting the target substance-magnetic particle complex to electrophoresis, whereby the target substance-magnetic particle-labeled substance complex and the unreacted second receptor-fixed labeled substance are separated from each other.

3. The method according to claim 1,
wherein the electrophoresis is carrier-free electrophoresis.

4. The method according to claim 1,
wherein the target substance amount in the biological sample is measured based on (i) a previously determined calibration curve of the signal intensity of the target substance-magnetic particle-labeled substance complex with respect to the target substance amount created using a target substance whose amount is known in advance, and (ii) the detected signal intensity of the target substance-magnetic particle-labeled substance complex.

5. The method according to claim 1,
wherein the labeled substance is at least one selected from the group consisting of a fluorescent substance, a radioactive isotope, an enzyme, or a redox substance.

6. The method according to claim 1,
wherein the biological sample is selected from the group consisting of blood, interstitial fluid, or urine.

* * * * *